United States Patent
Deeds

(10) Patent No.: US 9,707,325 B2
(45) Date of Patent: Jul. 18, 2017

(54) DRAINAGE SYSTEM WITH OCCLUSION MEMBER

(75) Inventor: Andrew C. Deeds, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1572 days.

(21) Appl. No.: 13/309,938

(22) Filed: Dec. 2, 2011

(65) Prior Publication Data

US 2013/0144269 A1    Jun. 6, 2013

(51) Int. Cl.
| | |
|---|---|
| *A61M 37/00* | (2006.01) |
| *A61M 1/00* | (2006.01) |
| *A61M 5/00* | (2006.01) |
| *A61M 29/00* | (2006.01) |
| *A61M 27/00* | (2006.01) |
| *A61M 3/02* | (2006.01) |

(52) U.S. Cl.
CPC ......... *A61M 1/0084* (2013.01); *A61M 3/0295* (2013.01)

(58) Field of Classification Search
CPC ........ A61M 37/00; A61M 5/00; A61M 29/00; A61M 1/00; A61M 27/00
USPC ........................................ 604/540, 541, 544
See application file for complete search history.

(56) References Cited

U.S. PATENT DOCUMENTS

| | | | |
|---|---|---|---|
| 3,416,532 A | 12/1968 | Grossman | 128/350 |
| 4,303,100 A * | 12/1981 | Kalb | E21B 21/106 137/853 |
| 4,634,443 A * | 1/1987 | Haber | 600/31 |
| 4,813,929 A | 3/1989 | Semrad | 604/51 |
| 5,188,618 A | 2/1993 | Thomas | |
| 5,279,567 A | 1/1994 | Ciaglia et al. | 604/117 |
| 5,458,583 A | 10/1995 | McNeely et al. | 604/96 |
| 5,509,909 A | 4/1996 | Moy | 604/281 |

(Continued)

FOREIGN PATENT DOCUMENTS

| | | | |
|---|---|---|---|
| DE | 3035243 A1 | 3/1982 | A61M 1/00 |
| GB | 2425483 A | 11/2006 | A61B 17/34 |
| WO | WO 01/12086 A1 | 2/2001 | A61B 17/34 |

OTHER PUBLICATIONS

European Search Report, dated Feb. 28, 2013, pp. 1-5, European Patent Application No. 12275177.9, European Patent Office, The Netherlands.

*Primary Examiner* — Tatyana Zalukaeva
*Assistant Examiner* — Ilya Treyger
(74) *Attorney, Agent, or Firm* — Brinks Gilson & Lione

(57) ABSTRACT

A medical device includes a tubular member having a distal end residing interiorly of the body of a patient, a proximal end extending exteriorly of the body, and a lumen extending therebetween. A first passageway extends along the tubular member between a distal end in fluid communication with the lumen, and a proximal end extending exteriorly of the body. A second passageway extends along the tubular member between a distal end located distal to the distal end of the first passageway, and a proximal end extending exteriorly of the body. An occlusion member is associated with the distal end of the second passageway. The occlusion member is movable between an occluded configuration and a non-occluded configuration for selectively occluding the lumen of the tubular member. When the lumen is occluded, a flushing fluid may be passed therethrough via the distal end of the first passageway.

20 Claims, 8 Drawing Sheets

(56) References Cited

U.S. PATENT DOCUMENTS

| | | | |
|---|---|---|---|
| 5,653,230 A | 8/1997 | Ciaglia et al. | 128/207.15 |
| 5,897,534 A | 4/1999 | Heim et al. | 604/267 |
| 6,183,450 B1 | 2/2001 | Lois | 604/267 |
| 6,517,519 B1 | 2/2003 | Rosen et al. | 604/164.06 |
| 6,692,508 B2 | 2/2004 | Wensel et al. | 606/159 |
| 6,905,484 B2 | 6/2005 | Buckman et al. | 604/174 |
| 7,036,510 B2 | 5/2006 | Zgoda et al. | 128/207.29 |
| 7,229,433 B2 | 6/2007 | Mullen | 604/164.04 |
| 7,854,728 B2 | 12/2010 | Boyle, Jr. | 604/267 |
| 7,951,243 B2 | 5/2011 | Boyle, Jr. et al. | 134/8 |
| 2004/0133232 A1 | 7/2004 | Rosenbluth et al. | 606/200 |
| 2006/0081260 A1 | 4/2006 | Eells et al. | 128/207.29 |
| 2006/0237022 A1 | 10/2006 | Chen et al. | 128/898 |
| 2009/0143722 A1 | 6/2009 | Kim | |
| 2009/0188531 A1 | 7/2009 | Boyle, Jr. et al. | 134/22.11 |
| 2009/0264833 A1 | 10/2009 | Boyle, Jr. | 604/257 |
| 2011/0040285 A1 | 2/2011 | Boyle | 604/540 |
| 2011/0040286 A1 | 2/2011 | Boyle, Jr. et al. | 604/540 |
| 2011/0152874 A1 | 6/2011 | Lyons | 606/108 |
| 2011/0152920 A1 | 6/2011 | Eckhouse et al. | 606/200 |
| 2012/0017943 A1 | 1/2012 | Boyle, Jr. et al. | 134/22.11 |

* cited by examiner

DRAINAGE SYSTEM WITH OCCLUSION MEMBER

BACKGROUND

The present disclosure relates generally to medical devices, and more particularly, to drainage systems including a drainage tube and an occlusion member for selectively closing the lumen of the drainage tube.

In the human body, the lungs are surrounded by the pleura. The pleura is a serous membrane which folds back upon itself to form a two membrane structure. The two membranes are known as the parietal pleura and the visceral pleura, respectively. The parietal (outer) pleura lines the chest wall, while the visceral (inner) pleura surrounds the lung. The space between the two pleurae layers is known as the pleural space or cavity, which space typically contains a thin layer of pleural fluid. This thin layer of fluid provides lubrication to enable the plurae layers to smoothly slide over one another during respiration.

Pleural effusion refers to a condition that occurs when an excess of fluid accumulates in the pleural space. Typically, such accumulation results from chest trauma experienced by the patient. The collection of air in the pleural space results in a condition commonly referred to as pneumothorax. The collection of blood in the pleural space results in a condition commonly referred to as hemothorax. Other fluids that may collect in the pleural space include serous fluid (hydrothorax), chyle (chylothorax), and pus (pyothorax). The presence of excessive amounts of fluids in the pleural space impairs the breathing ability of the patient by limiting the ability of the lungs to expand during inhalation.

In order to drain excess fluid, a chest tube may be inserted into the pleural space. Often the chest tube is inserted utilizing the well-known Seldinger technique. In the Seldinger technique, a needle is initially advanced into the pleural space. A wire guide is inserted through a bore of the needle, and the needle is thereafter removed, leaving the distal end of the wire guide positioned in the pleural space. A series of tapered dilators (such as three) are sequentially advanced (small to large) over the wire guide to dilate the tissue of the chest wall, and form an opening, or stoma, of desired size. After removal of the largest dilator, the chest tube, with inserter/obturator, is placed over the wire guide, and the distal end of the tube is directed into the pleural space.

During drainage of excess fluid, blood can clot in the chest tube inside the patient, impairing the drainage function of the chest tube. Consequently, fluid and/or blood can build up in the pleural space. Such build-up can restrict the full expansion of the lungs and lead to deleterious consequences, including potential death. When the chest tube is implanted and sterile, the end user can at times manipulate the chest tube to remove the blood clot, such as by squeezing the chest tube, bending the chest tube at several points, and/or sliding while squeezing the chest tube. The chest tube can be partially withdrawn in order to gain external access to the blood clot. However, this action violates the sterile internal environment of the chest tube, making the treated area more susceptible to infection. Further, the seal between the chest tube and the drainage system is broken, which can increase the risk of losing the physiological negative pressure inside the chest.

Thus, it would be desirable to provide drainage systems and methods of use thereof that effectively eliminate blockage or clogging of a drainage tube. It would be desirable if such action occurs while maintaining the drainage tube implanted within the patient in order to maintain a sterile environment. Further, it would be desirable if such systems and methods can permit periodic blockage removal, thereby reducing the risk of trauma around the drainage tube, which contributes to bleeding, tissue injury, and infection.

SUMMARY

The present invention addresses the problems of the prior art. In one form thereof, a medical device comprises a tubular member configured to have a distal end residing interiorly of the body of a patient and a proximal end extending exteriorly of the body of the patient. The tubular member has a lumen formed therein extending between the distal end and the proximal end. A first passageway extends along the tubular member extending between a distal end in fluid communication with the lumen, and a proximal end extending exteriorly of the body. A second passageway extends along the tubular member extending between a distal end located distal to the distal end of the first passageway, and a proximal end extending exteriorly of the body. An occlusion member is associated with the distal end of the second passageway, wherein the occlusion member is movable between an occluded configuration and a non-occluded configuration for selectively occluding the lumen of the tubular member.

In another form thereof, a drainage system comprises a tubular member having a distal end to reside within an interior body space of a patient and a proximal end to extend outside the body of the patient. The tubular member has a lumen formed therein extending between the distal and proximal ends of the tubular member. A first passageway formed therein extends between a distal end in fluid communication with the lumen and a proximal end extending outside the body. A second passageway formed therein extends between a distal end located distal to the distal end of the first passageway and a proximal end extending outside the body. An occlusion member is associated with the distal end of the second passageway. The occlusion member is movable between an occluded configuration and a non-occluded configuration for selectively occluding the lumen of the tubular member. A fluid source comprising an agent for removing debris formed along the lumen, is coupled to the first passageway.

In still another form thereof, a method is provided for clearing debris from a medical tube. A tubular member is positioned to extend between a body space within a body of a patient and a collection receptacle. The tubular member has a distal end residing within the body space and a proximal end extending outside the body of the patient. The tubular member has a lumen formed therein extending between the distal end and the proximal end of the tubular member. A first passageway is formed therealong extending between a first distal end in fluid communication with the lumen, and a first proximal end extending outside the body. A second passageway is formed therealong extending between a second distal end located distal to the distal end of the first passageway, and a second proximal end extending outside the body. An occlusion member is associated with the distal end of the second passageway, wherein the occlusion member is initially in a non-occluded configuration. The occlusion member is moved to an occluded configuration to occlude the lumen of the tubular member. A fluid is introduced through the first passageway into the lumen of the tubular member while the occlusion member is in the occluded configuration, wherein the fluid comprises an agent for removing debris disposed along the lumen. A negative pressure may be applied within the lumen of the tubular member to facilitate clearing of the debris from the lumen.

BRIEF DESCRIPTIONS OF THE DRAWINGS

DETAILED DESCRIPTION OF THE DRAWINGS AND THE PRESENTLY PREFERRED EMBODIMENTS

Figure 1:
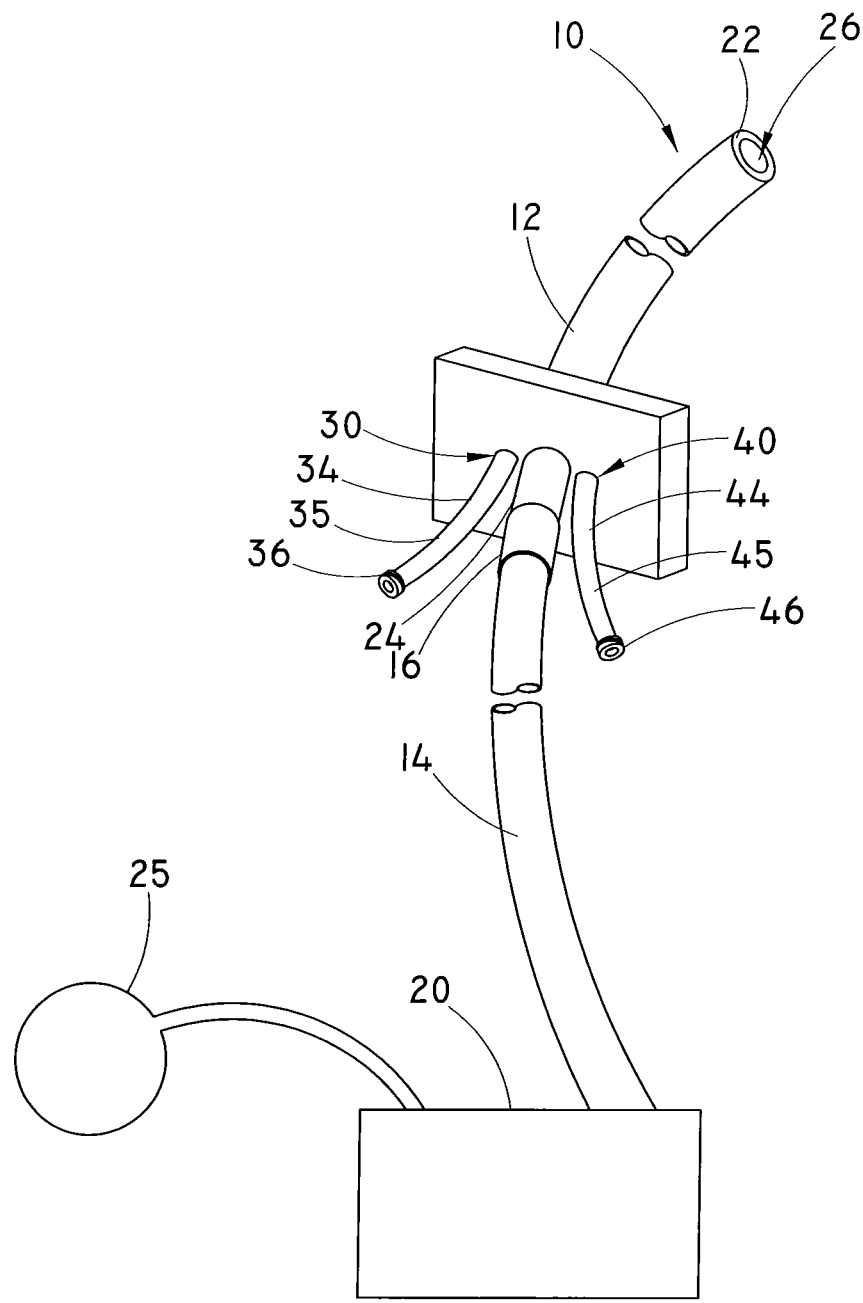
FIG. 1 illustrates a drainage system according to an embodiment of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. Like-referenced numerals are used throughout the Figures to designate similar components.

Throughout the specification, when referring to a medical device, or a portion of a medical device, the terms "distal" and "distally" shall denote a position, direction, or orientation that is generally toward, or in the direction of, the patient when the device is in use. The terms "proximal" and "proximally" shall denote a position, direction, or orientation that is generally away from the patient, or closer to the operator, during use of the device.

The drainage system described herein can be useful for drainage of spaces, vessels, cavities, lumens, ducts, and passageways of the body. When discussion of such spaces, vessels, cavities, lumens, ducts, passageways, etc., is made herein, these terms are used to describe such structures in general as found in the body of the patient, and are not limited to any one particular space, vessel, cavity, lumen, duct, passageway, etc. For convenience only, and not by way of limitation, the drainage system will at times be described herein for drainage of a "space" in the body, e.g., the pleural space.

FIG. 1 depicts one example of a drainage system 10 configured to drain fluids from a body space of a patient. The drainage system 10 can include one or more body tubes 12, one or more corresponding canister tubes 14, a coupling member 16 configured to couple the body tube 12 with the corresponding canister tube 14, and a collection receptacle, such as drainage canister 20. It can be appreciated that in some examples the body tube 12 and the canister tube 14 may be formed integrally from a single tube, and the coupling member may be omitted. The body tube 12 includes a distal end 22 that is configured to be inserted into the chest or other body space (or vessel, cavity, lumen, duct, passageway, etc.) and a proximal end 24 that extends outside of the body for coupling with the canister tube 14. If desired, the distal end 22 may be tapered. The body tube 12 is configured to provide a fluid path from the body space to the drainage canister 20 in order to facilitate the drainage of fluid from the body space.

A vacuum or other negative pressure source 25 can be coupled to the system 10 to form a closed-suction drainage system. The vacuum source 25 is provided to create low pressure in the drainage canister 20 in order to draw fluids out of the body space and into the drainage canister 20 via body tube 12 in well-known fashion. The system 10 can facilitate the clearing and/or removal of debris, such as, but not limited to, blood clots from within the drainage lumen 26 of the body tube 12. The presence of such debris can impair the ability of body fluids to pass through the lumen of the body tube 12.

Chest tubes are a common type of a body tube, and the remaining description will primarily be made with reference to chest tubes. However, it will be appreciated that the aspects and embodiments hereafter described can be applied directly or with minor and routine modifications to clear obstructive debris from other medical tubes used in different applications. Non-limiting examples include catheters and surgical drain tubes for draining fluid from other orifices (besides the pleural space), endotracheal tubes, feeding tubes, gastric tubes, and tubes for delivering material to or from the alimentary tract.

The body tube 12 may be formed of any materials commonly utilized for such purposes. Typically, the body tube 12 will be formed from a relatively rigid, clear polymer, such as polyvinylchloride (PVC). Those skilled in the art will appreciate that other polymers commonly employed for such purposes, such as polyurethane, are also suitable. The body tube 12 may have any dimensions typically provided with such tubes. For example, when the body tube is a chest tube, the tube 12 may have an outer diameter from about 8 to 36 French (2.7 to 12 mm), and an inner diameter from about 0.078 to 0.33 inch (2.0 to 8.4 mm). The body tube 12 may have a length from about 18 to 41 cm. In many cases, smaller French size chest tubes will have a smaller length, and larger French size tubes will have a greater length.

As with conventional body tubes, the body tube 12 may include one or more radiopaque stripes (not shown) along a length of the body tube, and if desired, may be provided with a hydrophilic coating along at least the distal portion of its outer surface. A plurality of side ports (not shown) can be provided along the body tube. When present, the side ports are typically positioned at the distal end of a body tube, and may have any conventional size, shape and dimensions. The side ports can be arranged along the distal end of the chest tube in any convenient manner, e.g., in a linear or in a spiral pattern. Body tubes, such as chest tubes, are well known in the art, and to the extent not specifically referenced herein, the body tube 12 may be provided with additional features known to be provided with such tubes.

Figure 2A:
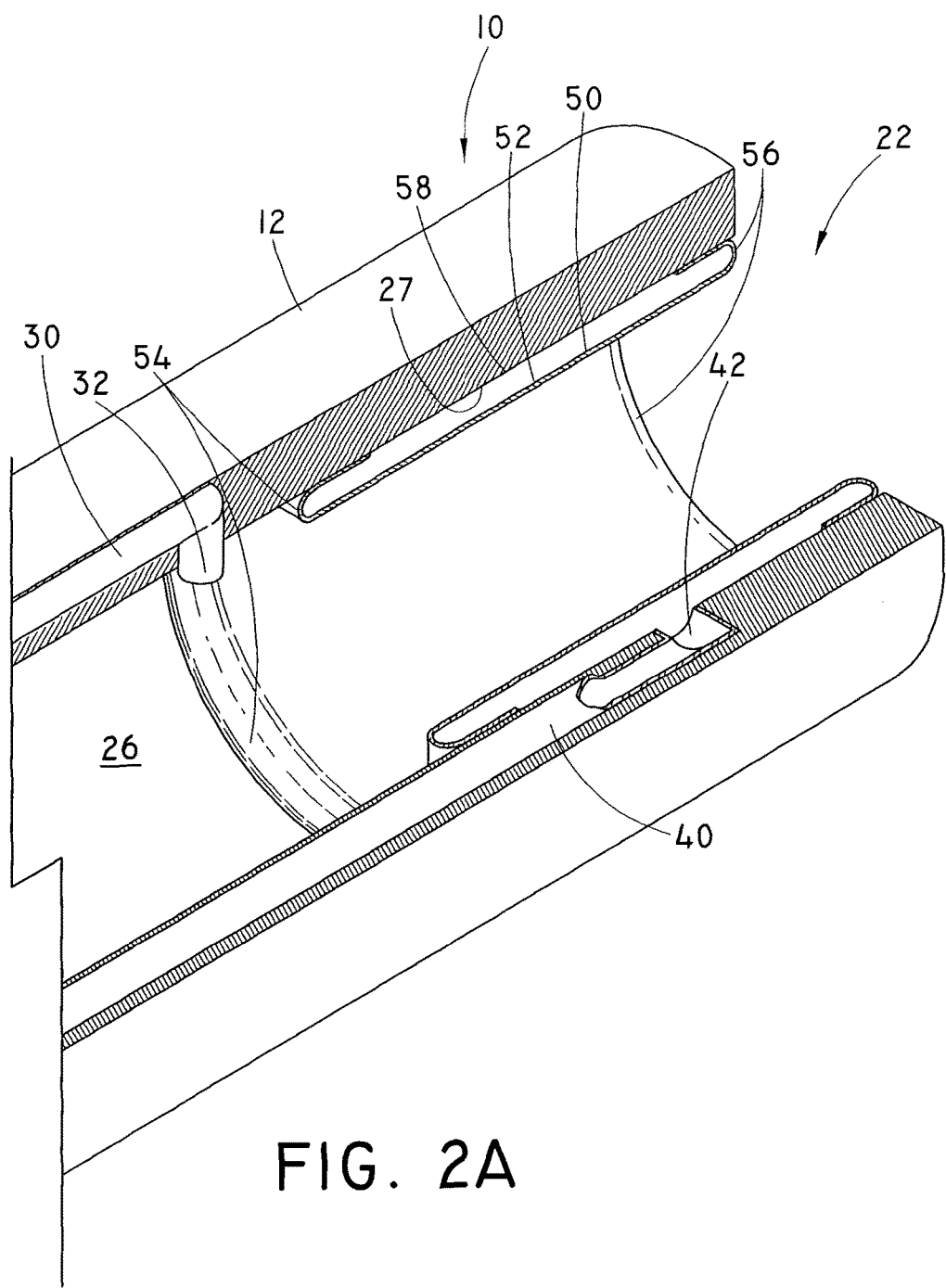
FIG. 2A depicts an enlarged partial cut-away of the distal end of the body tube of FIG. 1, illustrating the expandable member in a non-occluded configuration.
Figure 2B:
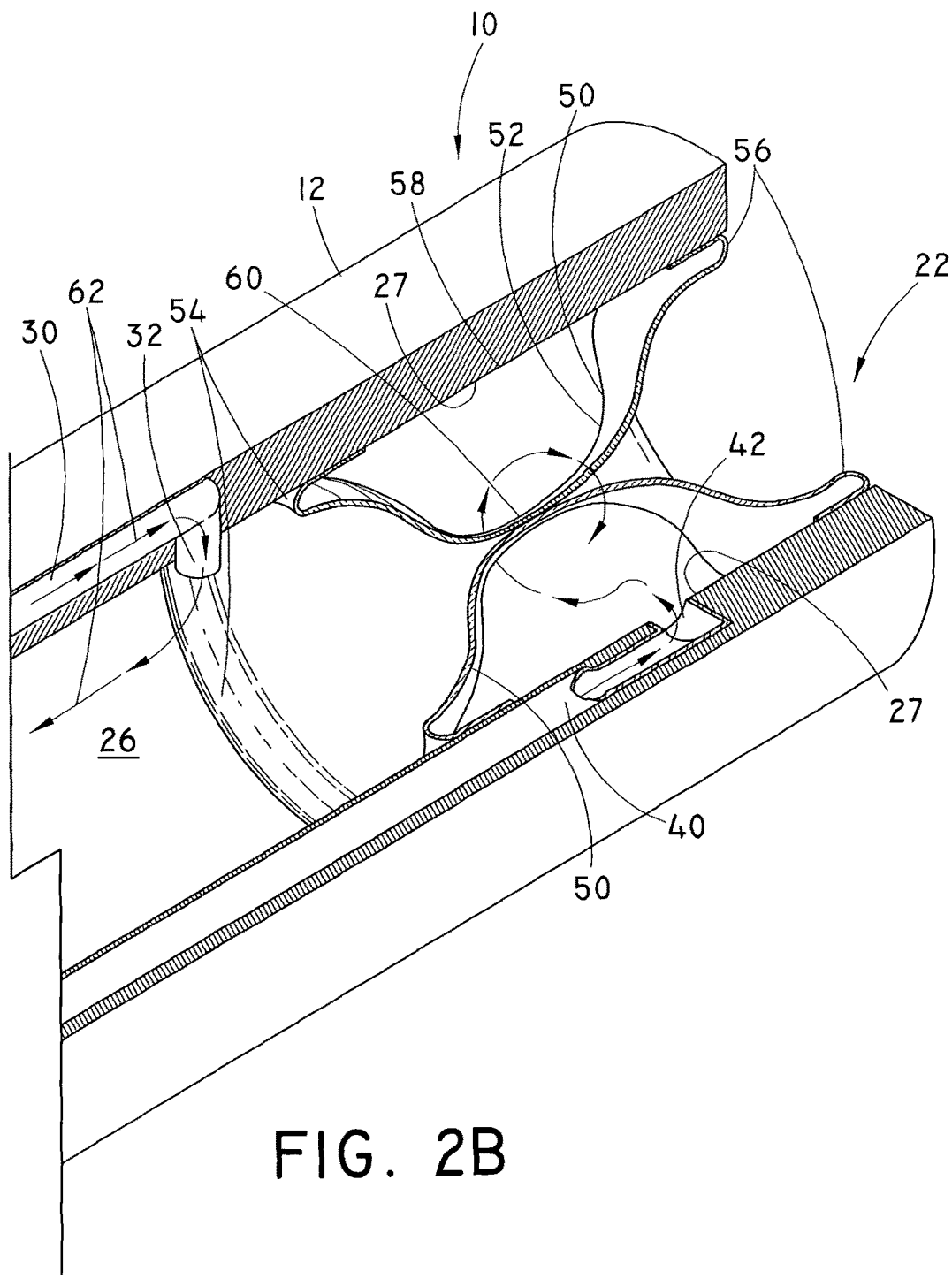
FIG. 2B depicts an enlarged partial cut-away of the distal end of the body tube as in FIG. 2A, illustrating the expandable member in an occluded configuration.

As shown in the embodiment of FIGS. 1, 2A, 2B, the body tube 12 includes longitudinal passageways therein. A first passageway 30 includes a distal end 32 in fluid communication with the drainage lumen 26, and a proximal end 34 that extends outside of the body. In one example, the proximal end 34 of the first passageway 30 is a tubular member 35 with a fluid coupling 36 at the end thereof.

A first fluid source, such as a syringe, etc., can be coupled to the fluid coupling 36, and may be utilized to deliver a fluid 62 through the first passageway 30 into the lumen 26 via passageway distal end 32. The fluid may be provided for flushing or irrigation purposes to assist in dislodging, dissolving, and/or breaking up debris formed within the drainage lumen 26, as described herein. The flushing or irrigation fluid may comprise, for example, water or a saline solution. Although the fluid may be a conventional saline solution, a heparinized saline solution may also be used. The heparinized saline may facilitate movement/dissolution of body fluids/clots, and may reduce clotting. As a further alternative, the fluid could also be a therapeutic agent. One non-limiting example of a therapeutic agent is an anti-thrombolytic agent (e.g., stryptokinase or urokinase) for use in breaking down clots. Another example of a therapeutic agent is an antibiotic agent for treatment of infection. Those skilled in the art will appreciate that other known agents may be used for a therapeutic or a diagnostic purpose. When not used for transmission of a flushing or irrigation fluid, or a therapeutic or diagnostic agent as described herein, first passageway 30 may also be used as a conduit to deliver an agent for any conventional medical treatment from proximal end 34 to the outside environment of the body cavity beyond the distal end opening of the drainage lumen.

A second passageway 40 includes an open distal end 42, and a proximal end 44. Proximal end 44 extends outside the body of the patient, and is configured for communication with an occlusion member. In one example, the occlusion member is an expandable bladder-type member 50 circumferentially positioned along the inner surface 27 of the distal portion of body tube 12. The proximal end 44 of the second passageway 40 may be a tubular member 45 with a fluid coupling 46 at the end thereof. A second fluid source, such as a syringe, bulb, balloon, etc., can be coupled to the fluid coupling 46 in conventional fashion. This fluid source may be utilized to deliver fluid through passageway distal end 42 for inflation of the expandable member 50.

Inflation of the expandable member 50 through distal end 42 as shown in FIG. 2B occludes the distal portion of the drainage lumen 26. Once the drainage lumen 26 is occluded as shown, the flushing or irrigation fluid may be introduced into the lumen via first passageway 30 (as shown by the arrows) for dislodging, dissolving, and/or breaking up the debris formed within the drainage lumen 26. To this end, the distal end 42 of the second passageway 40 can be located distal to the distal end 32 of the first passageway 30. The inflation fluid may comprise air, water, saline or other conventional fluids commonly used in the medical arts used for inflating an expandable member.

As shown in the embodiment of FIGS. 2A-2B, expandable member 50 for occluding lumen 26 may comprise a cuff 52. In the embodiment shown, the cuff 52 includes a proximal end 54 and a distal end 56. Respective proximal and distal ends 54, 56 are sealed to the inner surface 27 of the body tube 12 in conventional manner, e.g., by heat bonding, ultrasonic welding, adhering with a compatible adhesive, etc. In one embodiment, cuff 52 may have a length of about 5 to 15 mm along the inner body tube surface 27. Those skilled in the art will appreciate that this dimension is only one example, and that other dimensions may be appropriate for a particular application.

An intermediate inflation region 58 is disposed axially between cuff proximal end 54 and distal end 56. Unlike proximal and distal ends 54, 56, intermediate region 58 remains unattached to the inner body tube surface 27. The distal end 42 of the second passageway 40 is positioned at a location proximate the intermediate region 58, such that a suitable fluid pressure within the intermediate location causes inward radial movement or expansion of the intermediate region 58. As a result of the inward radial expansion, a constriction, or seal, 60 is formed in the drainage lumen 26, as shown in FIG. 2B. The constriction 60 is suitable to at least substantially, if not totally, occlude a distal portion of drainage lumen 26, thereby preventing fluid 62 from the first fluid source via the distal end 32 of the first passageway 30 from exiting out from the distal end opening of the drainage lumen 26 during flushing or irrigation. As a result, this fluid 62 flows in the direction shown by the arrows in FIG. 2B for dislodging, dissolving, and/or breaking up debris formed along the drainage lumen 26, as described.

Figure 3:
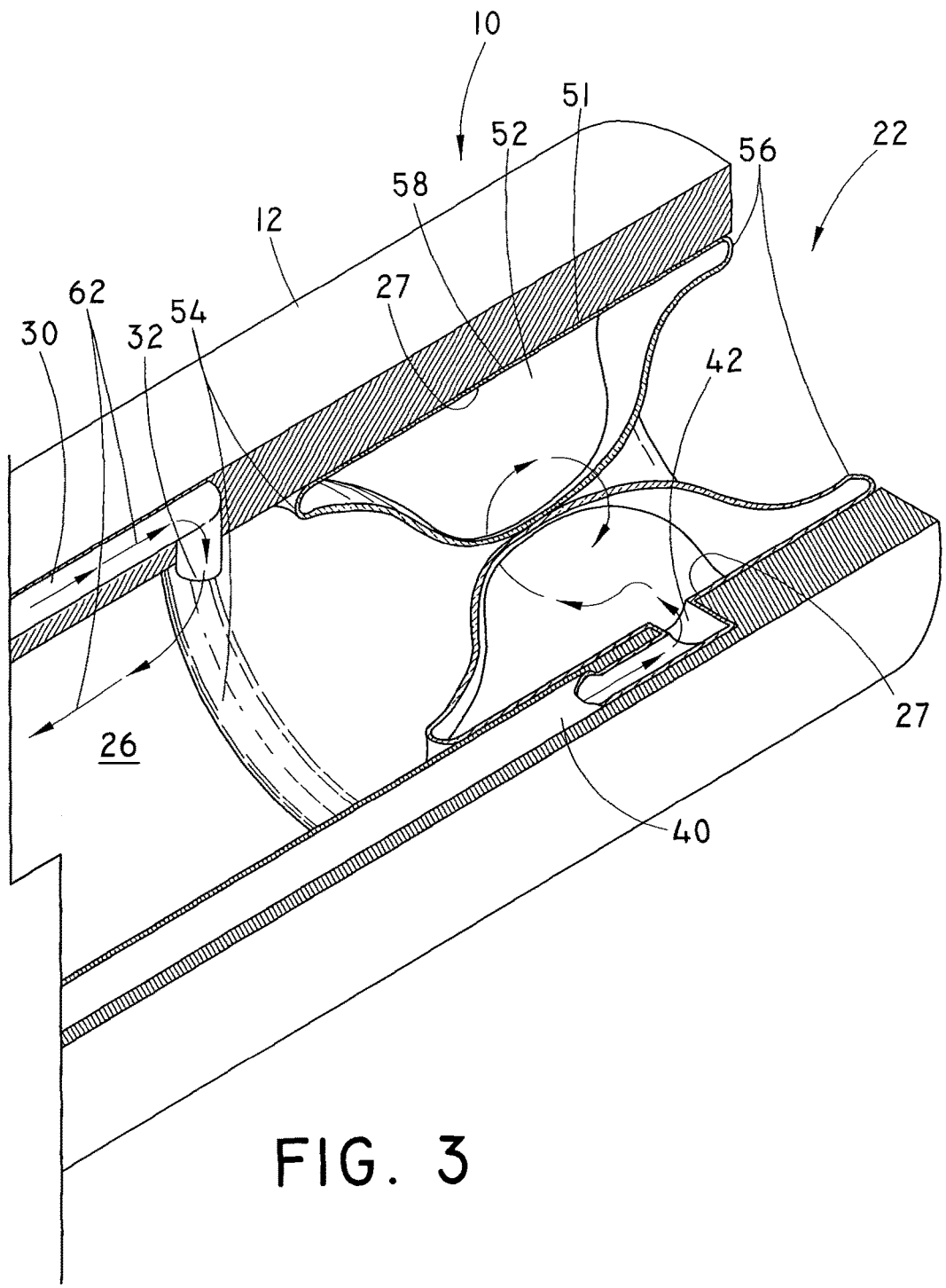
FIG. 3 depicts an enlarged partial cut-away of a variation of the embodiment of FIGS. 2A and 2B.

FIG. 3 illustrates a variation of the embodiment of FIGS. 2A-2B. Rather than a cuff, in this variation the expandable member is in the nature of an expandable balloon 51. The expandable balloon may be formed of any conventional balloon material in use in the medical arts, such as silicone.

Those skilled in the art will appreciate that there are many ways to form passageways 30, 40 in body tube 12. Preferably, passageways 30, 40 are formed in the wall of body tube 12. Such passageways may be formed by any conventional techniques, such as insert molding, extrusion, etc., and are dimensioned to allow sufficient fluid to pass therethrough to carry out the actions described above. For example, a tubular body may have a wall thickness of about 2 to 5 mm. In this event, passageways 30 and 40 may each have a diameter of about 0.5 to 2 mm. Those skilled in the art will appreciate that the dimensions provided herein are only examples, and that the dimensions of the body tube, passageways, etc., may be varied as desired for a particular application.

Figure 4A:
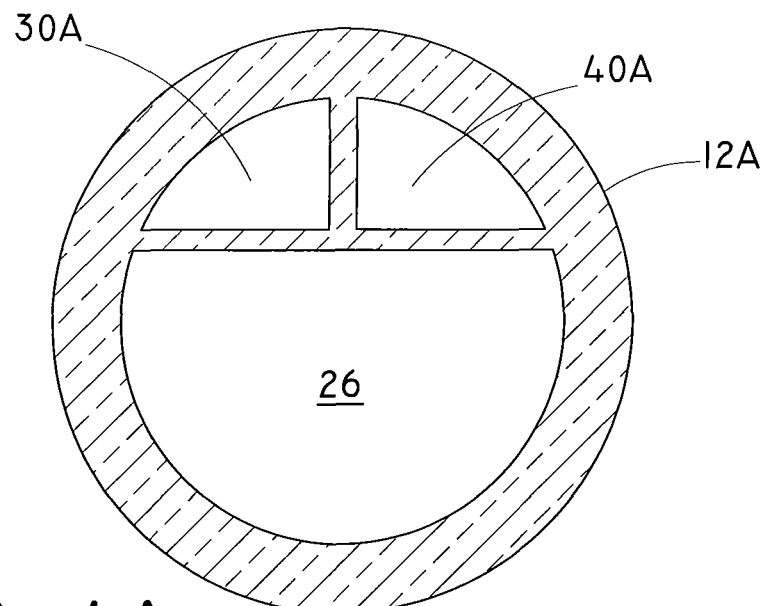
FIGS. 4A and 4B illustrate enlarged sectional views of alternative embodiments of the body tube and passageways.
Figure 4B:
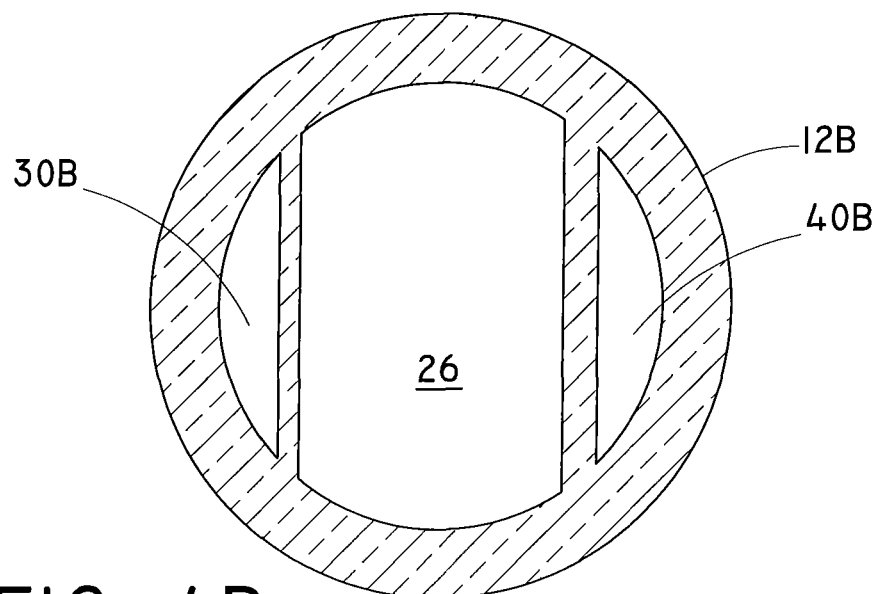

Although passageways 30, 40 have been shown and described herein as extending through opposing walls of body tube 12, this arrangement is not exclusive. For example, FIGS. 4A and 4B illustrate sectional views of alternative embodiments of body tube 12A, 12B wherein respective passageways 30A, 40A (FIG. 4A) and 30B, 40B (FIG. 4B) are branched off from body tube lumen 26. Those skilled in the art will appreciate that other arrangements of passageways for carrying fluids as described herein may be substituted.

Figure 5:
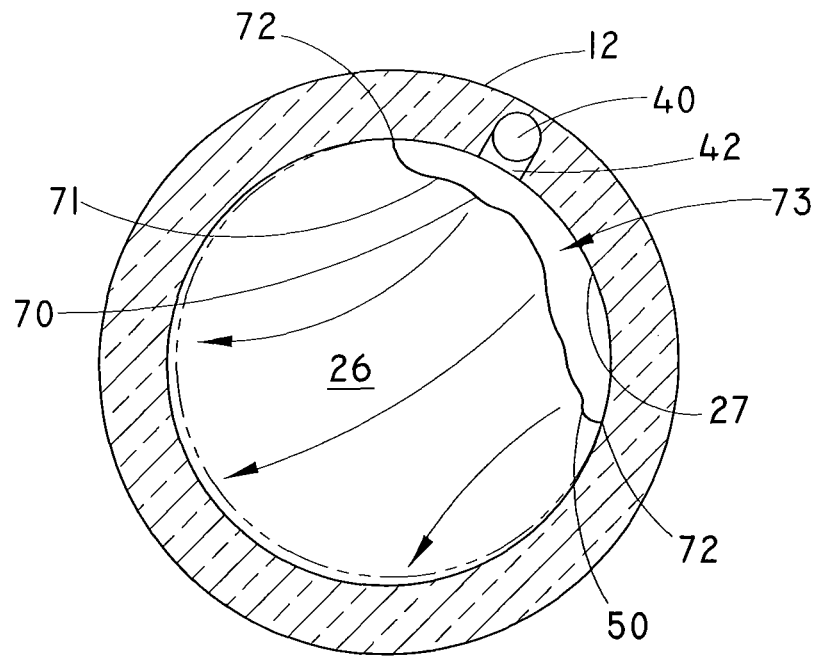
FIG. 5 illustrates an enlarged sectional view of the body tube, showing another embodiment of an expandable member.

FIG. 5 illustrates another example of the expandable member. In this embodiment, the expandable member is a balloon 70. The balloon is shown in a non-expanded configuration in the sectional view depicted in the figure. In this case, longitudinal edges 72 of the balloon material 71 are sealed along a length of inner surface 27 of the body tube 12, and the uninflated balloon is positioned along one side of the inner surface. The distal end 42 of the second passageway 40 is positioned at a location proximate the intermediate region 73 of the balloon material 71 between the sealed edges 72. Balloon 70 may have a length, for example, of about 5 to 15 mm along the inner body tube surface 27. Those skilled in the art will appreciate that this dimension is only one example, and that other dimensions may be appropriate for a particular application. First passageway 30 is proximal of balloon 70, as shown in FIGS. 2A, 2B so that fluid 62 flows in the same manner as shown and described with reference to the embodiment of FIG. 2B.

A suitable fluid pressure introduced through distal end 42 of second passageway 40 within the intermediate region 73 can facilitate expansion of the intermediate balloon region 73 (as shown by the arrows) from the non-expanded configuration as shown, to an expanded configuration across the drainage lumen 26 (shown in dashed lines in FIG. 5). The expanded balloon forms a seal across the lumen. The inflated diameter of the balloon is selected in view of the size of the drainage lumen. The fluid pressure can be provided with the introduction of inflation fluid via the fluid coupling 46 and second passageway 40. The seal provided by the expanded balloon 70 is suitable to occlude the drainage lumen, preventing substantially any fluid 62 from the distal end of the first passageway 30 from exiting out from the distal end opening of the drainage lumen 26 during flushing or irrigation.

The expandable members (e.g., cuff, bladder, balloon) for use herein can be made of any conventional materials used in construction of expandable members for medical purposes. Examples of such materials include, but are not limited to, polyethylene terephthalate (PET), polyamide (nylon), polyether block amide, polyurethane, polyethylene, low-pressure elastic materials such as silicone, or higher pressure inelastic materials. Such materials can conveniently have an average burst pressure of, for example, between about ten and twenty bars. As a still further variation, the respective positions of the second passageway and the expandable member may be modified such that the expandable member is located external to the drainage lumen at the distal end opening, rather than internally as shown.

Figure 6:
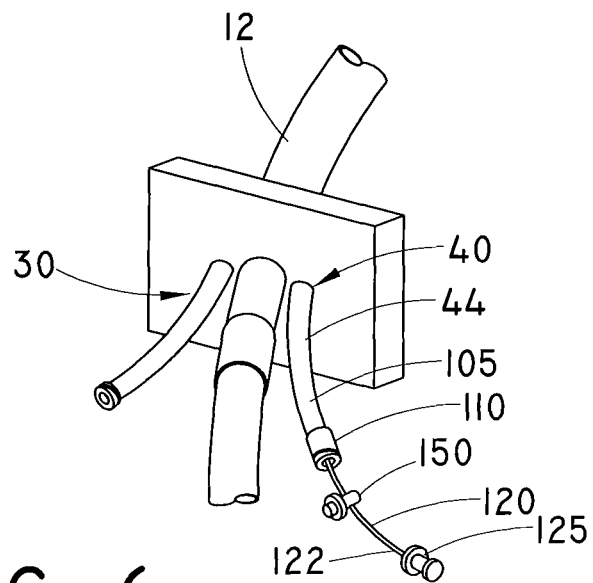
FIG. 6 illustrates the proximal end portion of another embodiment of a drainage system.
Figure 7A:
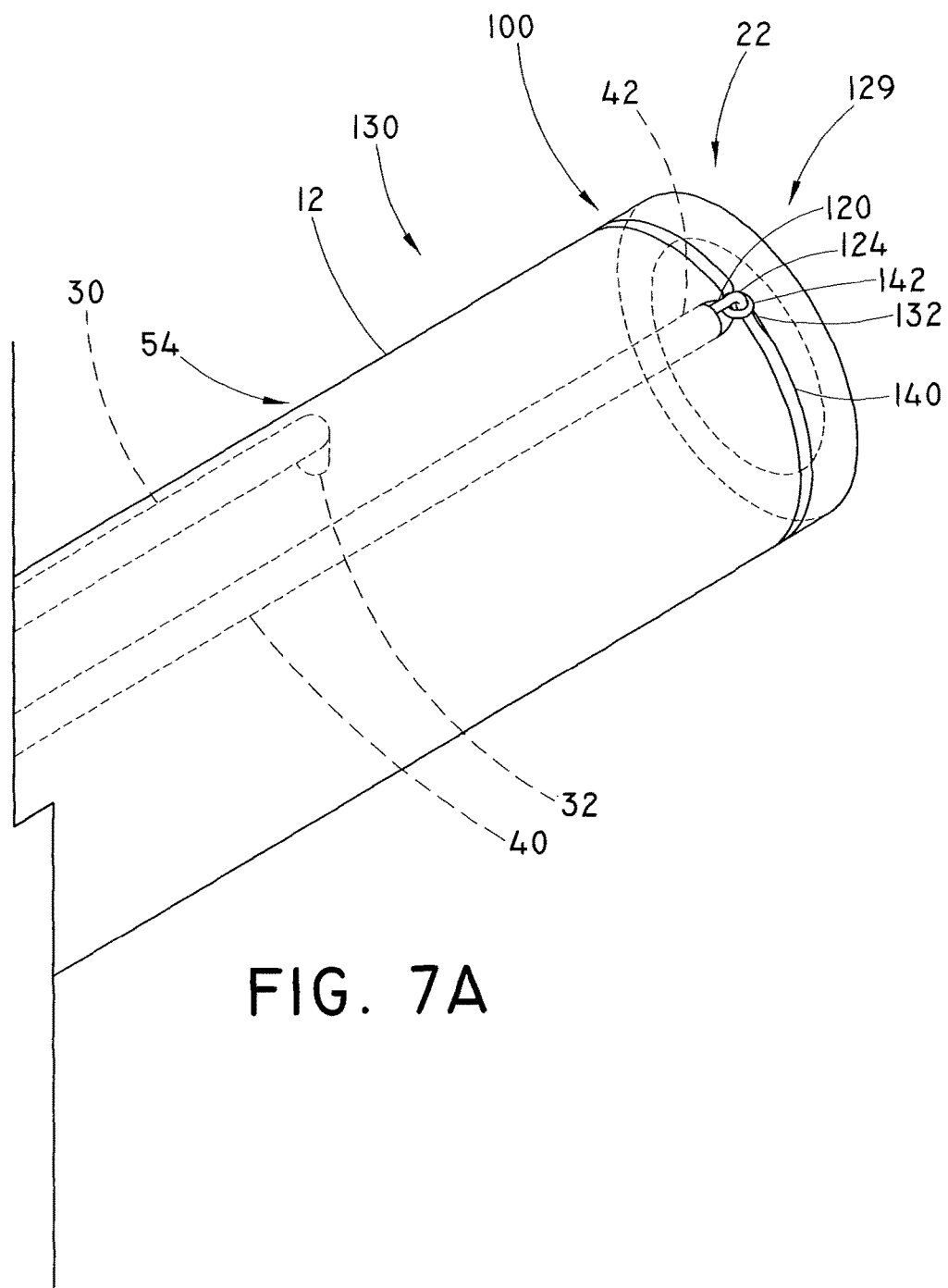
FIG. 7A illustrates an enlarged view of the distal end of the body tube of the embodiment of FIG. 6, illustrating the constriction member in a non-occluded configuration.
Figure 7B:
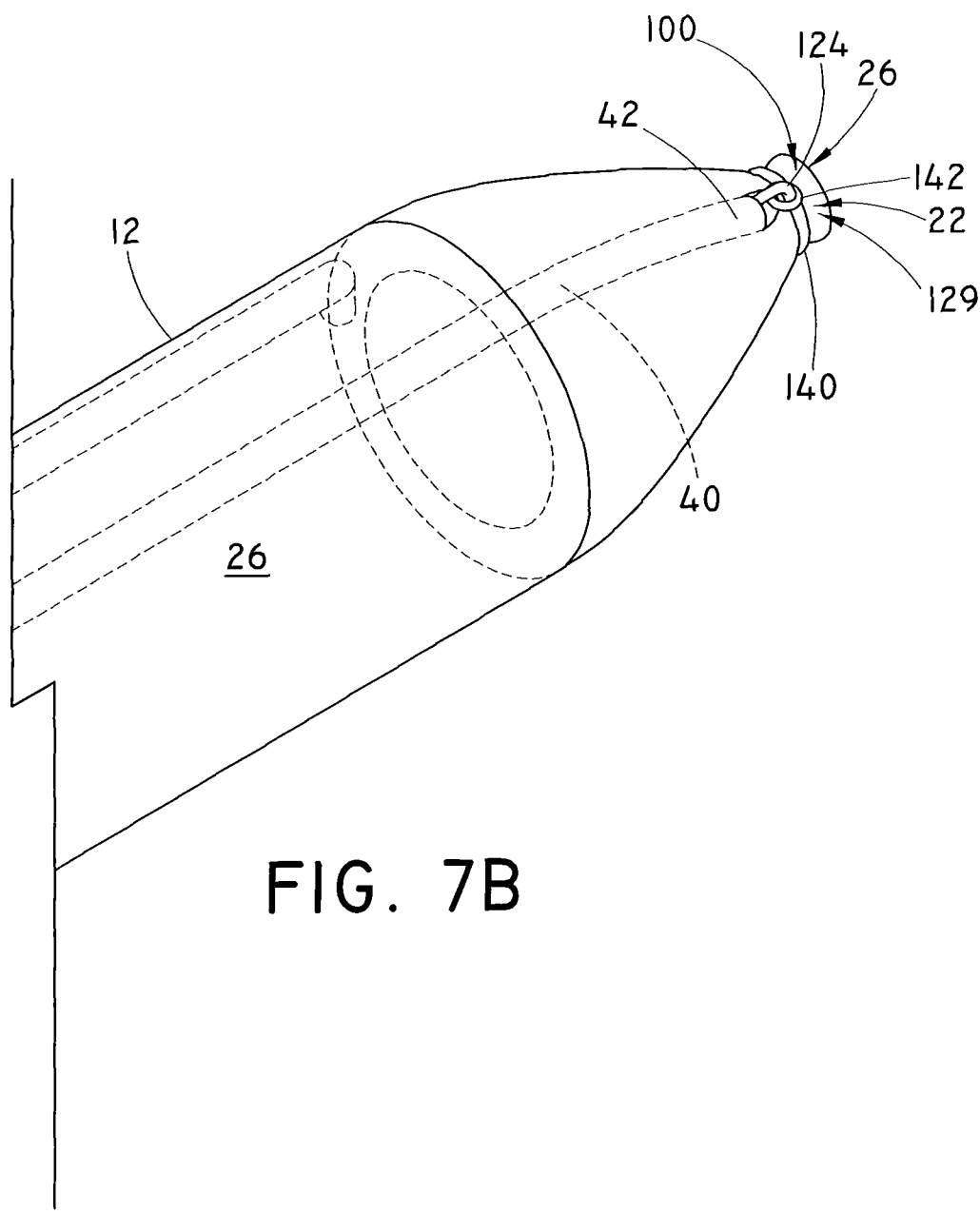
FIG. 7B illustrates the enlarged view of the distal end of the body tube as in FIG. 7A, illustrating the constriction member in an occluded configuration.

FIGS. 6-7B illustrate another example of a body tube having an occlusion member. In this example, the occlusion member comprises a constriction device 100 for constricting a distal end portion of lumen 26. In the non-limiting embodiment shown, the constriction device 100 includes an elongated body 120 having a proximal end 122 and a distal end 124. A snare member 140 is coupled to the distal end 124 of the elongated body 120.

FIG. 6 illustrates the proximal end 44 of the second passageway 40 as a tubular member 105. The second passageway 40 may have a hemostatic seal 110 provided at the end of tubular member 105 to inhibit fluid loss therethrough. Elongated body 120 is sized to extend through the second passageway 40, wherein proximal end 122 exits out of the proximal end of second passageway 40 through the hemostatic seal 110. The body 120 may comprise a solid member, a tubular member, or any combination thereof, as made from, e.g., a metal, a metal alloy, a polymer, or a composite material that may include a combination of the foregoing. The body 120 is configured to have sufficient axial force transmission from the proximal end 122 to the distal end 124 to permit pushing or pulling of the body 120 from the proximal end. Proximal end 122 can be provided with a handle 125 to facilitate gripping of the body 120 during operation thereof.

FIGS. 7A-7B depict the distal end 22 of the body tube 12. These figures illustrate one manner in which the distal end 129 of an occlusion member, such as constriction device 100, is configured to move between a constricted configuration for forming a seal within the drainage lumen, and a non-constricted configuration. As shown, the distal end 42 of the second passageway 40 can extend through the distal end of body tube 12, or through the distal outer surface 130 of the body tube. The distal end 124 of the elongated body 120 is coupled to a snare member 140. The snare member 140 circumferentially encloses the body tube 12. The circumference of snare member 140 is reduced, or constricted, (FIG. 7A to FIG. 7B) upon application of a withdrawing force to the proximal end 122 of the elongated body 120. A groove or channel 132 may be formed in the outer surface 130 of the body tube 12 to contain and guide the radial constriction of the snare member 140.

In one example, the elongated body 120 and the snare member 140 may be formed integrally from a single element. The distal end 124 of the elongated body 120 can be looped, and a length of the elongated body 120 adjacent to the looped distal end can be wrapped around the circumference of the body tube 12 to define the snare member 140. A portion 142 of the elongated body 120 can be inserted within the opening formed by the looped distal end, and redirected to the distal end 42 of the second passageway 40.

Upon application of a withdrawing force to the proximal end 122 of the elongated body 120, the force can be axially translated to the distal end 124 such that snare member 140, and thereby body tube 12, are constricted to the configuration shown in FIG. 7B. A locking or clamping device 150, such as a hemostat, can be provided at the proximal end of the elongated body 120 to selectively retain the relative position of the elongated body 120 in the constricted configuration. A flushing or irrigation fluid may then be introduced into the lumen via distal end 32 of the first passageway 30 for dislodging, dissolving, and/or breaking up debris formed within the drainage lumen proximal of distal end 32, as described above. In one example, the locking device 150 is fixedly attached around the elongated body 120, against the proximal end of the member 105. The locking device is removable from the elongated body to allow the elongated body to move relative to the second passageway and to permit the distal end 129 to move to the non-constriction configuration.

The following description will describe one example of the operation of the system, in this case as a drainage chest tube. As noted above, the medical tube need not be a chest tube, and the following example is only intended to describe one possible use of the system.

In order to drain excess fluid, the chest tube may be inserted into the pleural space utilizing various techniques, such as the well-known Seldinger technique. For example, in the Seldinger technique, a needle having a bore therethrough is initially advanced into the pleural space. A wire guide is inserted through the bore of the needle, and the needle is thereafter removed, leaving the distal end of the wire guide positioned in the pleural space. A series of tapered dilators (such as three) are sequentially advanced (small to large) over the wire guide to dilate the tissue of the chest wall, and form an opening, or stoma, of desired size. After removal of the largest dilator, the chest tube, which can have an inserter/obturator, is placed over the wire guide, and the distal end of the chest tube is directed into the pleural space. The proximal end of the chest tube remains outside the body.

After the distal end of the chest tube is positioned at the desired location of the pleural space, the proximal end of the chest tube can be coupled to the canister tube via a coupling device in a sealed manner as conventionally performed. A negative pressure source, such as a vacuum or other suction source, is coupled to the chest tube. The negative pressure source can draw fluids out of the pleural space and into the drainage canister to be disposed of or collected, and also to sustain the normal physiologic negative pressure within the chest.

Periodically, the occlusion member, according to the examples described herein, can be activated to clear occlusions or other debris from the drainage lumen of the chest tube. A fluid 62 is introduced through the first passageway 30 to flush through the drainage lumen, e.g., as shown in FIG. 2B. As the fluid drains through lumen 26 in the proximal direction, the fluid will dislodge, dissolve, and/or breakup debris, e.g., blood clots, mucus, etc., formed within the drainage lumen 26. The negative pressure source assists in drawing the excess fluid and the debris from the drainage lumen and into the drainage canister to be disposed of or collected.

The occlusion member can be located anywhere along the length of the drainage lumen of the body tube. However, as described herein, it is preferred that the occlusion member is positioned at or near the distal end of the drainage lumen so that as large an area as possible of the inner surface of the drainage lumen can be cleared via the flushing fluid.

The system described herein can be used in conjunction with other medical body tubes used to provide fluid communication between a location within a human or animal body and an external apparatus or environment, either to drain fluid or other material from the body (e.g. chest tube, urinary catheter or other drainage tube) or to deliver material from outside the body (e.g. NG-tube or intubation tube). Thus, for example, a urinary catheter or tube may include the arrangements described herein to clear the catheter of obstructions (e.g., salt crystals, blood clots, etc.) that may form therein.

Drawings in the figures illustrating various embodiments are not necessarily to scale. Some drawings may have certain details magnified for emphasis, and any different numbers or proportions of parts should not be read as limiting, unless so designated in the present disclosure. Those of skill in the art will appreciate that medical procedures not expressly described and/or illustrated herein may be practiced within the scope of the present invention. It is therefore intended that the foregoing detailed description be regarded as illustrative rather than limiting. It should be understood that the following claims, including all equivalents, are intended to define the spirit and scope of this invention.

I claim:

1. A medical device comprising:
 a tubular member configured to have a distal end residing interiorly of the body of a patient and a proximal end extending exteriorly of the body of the patient, the tubular member having a lumen formed therein extending between an opening at said distal end and said proximal end, a first passageway extending along said tubular member extending between a distal end in fluid communication with the lumen and a proximal end extending exteriorly of the body, a second passageway extending along said tubular member extending between a distal end located distal to the distal end of the first passageway and a proximal end extending exteriorly of the body, and an occlusion member associated with the distal end of the second passageway, wherein the occlusion member is movable between an occluded configuration and a non-occluded configuration for selectively occluding the lumen of the tubular member;
 wherein the occlusion member, while in both the occluded configuration and the non-occluded configuration, is positioned about an entire circumference of the tubular member, so that when the occlusion member in the non-occluded configuration, the lumen of the tubular member thereby extends axially through the occlusion member; and
 wherein the occlusion member, when moving to the occluded configuration, is movable radially inward about the entire circumference of the tubular member to form a seal within the lumen of the tubular member by a first portion of the occlusion member pressing against a second portion of the occlusion member.

2. The device of claim 1, wherein the proximal end of the first passageway includes a fluid coupling.

3. The device of claim 1, wherein the occlusion member comprises an expandable member.

4. The device of claim 3, wherein the expandable member comprises a tubular cuff attached along an inner surface of the tubular member and expandable for occluding said tubular member lumen.

5. The device of claim 4, wherein the tubular cuff includes a proximal seal distal to the distal end of the first passageway, a distal seal, and an intermediate region, wherein in response to pressurization of the intermediate region via the second passageway, the intermediate region of the cuff is movable radially inward to the occluded configuration.

6. The device of claim 1, wherein the distal end of the second passageway is disposed on an outer surface of the tubular member.

7. The device of claim 6, wherein the occlusion member comprises a constriction device.

8. The device of claim 7, wherein the constriction device comprises a distal portion of the tubular member and an elongated body having a distal end and a loop segment at the distal end of the elongated body, wherein in response to movement of the elongated body in the proximal direction, a cross-sectional area of the loop segment decreases to define said occluded configuration.

9. A drainage system comprising:
 a tubular member having a distal end to reside within an interior body space of a patient and a proximal end to extend outside the body of the patient, the tubular member having a lumen formed therein extending between an opening at the distal and proximal ends of the tubular member, a first passageway formed therein extending between a distal end in fluid communication with the lumen and a proximal end to extend outside the body, a second passageway formed therein extending between a distal end located distal to the distal end of the first passageway and a proximal end to extend outside the body, and an occlusion member associated with the distal end of the second passageway, wherein the occlusion member is movable between an occluded configuration and a non-occluded configuration to selectively occlude the lumen of the tubular member wherein the occlusion member, while in both the occluded configuration and the non-occluded configuration, is positioned about an entire circumference of the tubular member, so that when the occlusion member in the non-occluded configuration, the lumen of the tubular member thereby extends axially through the occlusion member, and wherein the occlusion member, when moving to the occluded configuration, is movable radially inward about the entire circumference of the tubular member to form a seal within the lumen of the tubular member by a first portion of the occlusion member pressing against a second portion of the occlusion member; and a fluid source coupled to the first passageway, the fluid source comprising an agent for removing debris formed along the lumen.

10. The system of claim 9, comprising a negative pressure source in communication with the lumen of the tubular member for drawing a body fluid through said lumen, and a collection receptacle positioned for receiving said body fluid.

11. The system of claim 9, wherein the occlusion member comprises an expandable member in communication with the distal end of the second passageway.

12. The system of claim 11, further comprising a second fluid source coupled to the second passageway, the second fluid source comprising an inflation fluid for said expandable member.

13. The system of claim 9, wherein the distal end of the second passageway is disposed along an outer surface of the tubular member, and the occlusion member comprises a constriction device.

14. The system of claim 13, wherein the constriction device includes an elongated body extending along the second passageway and a loop segment coupled to the elongated body surrounding the outer surface of the tubular member, wherein in response movement of the elongated body, a cross-sectional area of the loop segment decreases to form the occluded configuration.

15. A method of clearing debris from a medical tube, comprising:
positioning a tubular member to extend between a body space within a body of a patient and a collection receptacle, the tubular member having a distal end residing within the body space and a proximal end extending outside the body of the patient, the tubular member having a lumen formed therein extending between an opening at the distal end and the proximal end of the tubular member, a first passageway formed therealong extending between a first distal end in fluid communication with the lumen and a first proximal end extending outside the body, a second passageway formed therealong extending between a second distal end located distal to the distal end of the first passageway and a second proximal end extending outside the body, and an occlusion member associated with the distal end of the second passageway, wherein the occlusion member is in a non-occluded configuration;
moving the occlusion member to an occluded configuration from the non-occluded configuration to occlude the lumen of the tubular member wherein the occlusion member, while in both the occluded configuration and the non-occluded configuration, is positioned about an entire circumference of the tubular member, so that when the occlusion member in the non-occluded configuration, the lumen of the tubular member thereby extends axially through the occlusion member, and wherein the occlusion member, when moving to the occluded configuration, is movable radially inward about the entire circumference of the tubular member to form a seal within the lumen of the tubular member by a first portion of the occlusion member pressing against a second portion of the occlusion member; and
introducing a fluid through the first passageway into the lumen of the tubular member while the occlusion member is in the occluded configuration, wherein the fluid comprises an agent for removing debris disposed along the lumen.

16. The method of claim 15, further comprising applying a negative pressure within the lumen of the tubular member to facilitate clearing of the debris from the lumen.

17. The device of claim 5, wherein the first portion and the second portion of the occlusion member are defined by the intermediate region of the cuff.

18. The device of claim 7, wherein the distal end of the tubular member has a smaller cross-sectional area when the constriction device is in the occluded configuration than when the constriction device is in the non-occluded configuration.

19. The device of claim 8, wherein the first portion and the second portion of the occlusion member are defined by a circumferential inner surface of the distal portion of the tubular member.

20. The device of claim 1, wherein the occlusion member is located at the distal end.

* * * * *